United States Patent
Baniasadi et al.

(10) Patent No.: US 11,883,607 B2
(45) Date of Patent: *Jan. 30, 2024

(54) PLATFORM INSERT FOR BOWL, BOWL WITH PLATFORM, AND METHODS OF USING THE SAME

(71) Applicants: AUGUSTA UNIVERSITY RESEARCH INSTITUTE, INC., Augusta, GA (US); Georgia Southern University Research and Service Foundation, Inc., Statesboro, GA (US)

(72) Inventors: Mahmoud Baniasadi, Portland, OR (US); Cargill H Alleyne, Jr., Martinez, GA (US)

(73) Assignees: AUGUSTA UNIVERSITY RESEARCH INSTITUTE, INC., Augusta, GA (US); GEORGIA SOUTHERN UNIVERSITY RESEARCH AND SERVICE FOUNDATION, INC., Statesboro, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/689,575

(22) Filed: Mar. 8, 2022

(65) Prior Publication Data

US 2022/0184340 A1 Jun. 16, 2022

Related U.S. Application Data

(63) Continuation of application No. 16/540,628, filed on Aug. 14, 2019, now Pat. No. 11,298,503.

(Continued)

(51) Int. Cl.
*A61M 25/00* (2006.01)
*B65D 25/10* (2006.01)
*B65D 85/04* (2006.01)

(52) U.S. Cl.
CPC ......... *A61M 25/002* (2013.01); *B65D 25/107* (2013.01); *B65D 85/04* (2013.01)

(58) Field of Classification Search
CPC ............ A61M 25/002; A61M 25/0041; A61M 25/0113; B65D 85/04; B65D 25/107; B65D 41/0428; A61B 50/30

(Continued)

(56) References Cited

U.S. PATENT DOCUMENTS

| 5,738,213 A | 4/1998 | Whiting et al. |
| D433,130 S | 10/2000 | Cude et al. |

(Continued)

FOREIGN PATENT DOCUMENTS

WO 98/56687 12/1998

OTHER PUBLICATIONS

Bastos Viegas Guidewire Bowl, http://www.bastosviegas.com/recipiente-fio-guia, as retrieved on Jul. 19, 2018.

*Primary Examiner* — Rafael A Ortiz
(74) *Attorney, Agent, or Firm* — Smith, Gambrell & Russell; Ryan A. Varnum

(57) ABSTRACT

A filament platform insert for insertion into a bowl includes a plurality protruding stages and a plurality of recesses that are each formed in arcuate shapes to form a plurality of arcuate filament channels. An access channel extending along the platform insert, between a top and bottom, and between a rear and front, provides access for insertion of a finger or tool for manipulating an endovascular filament stored in the filament channel. The platform insert is dimensioned such that alignment of multiple such platforms will form filament raceways within a bowl for the coiled reception and storage of multiple endovascular filaments, with each filament reliably isolated from one another. In an alternative configuration, an endovascular filament bowl (Continued)

may be made to have the filament platform as a monolithic component thereof.

19 Claims, 7 Drawing Sheets

Related U.S. Application Data

(60) Provisional application No. 62/764,781, filed on Aug. 16, 2018.

(58) Field of Classification Search
USPC .......................... 206/364, 557, 564, 388, 339
See application file for complete search history.

(56) References Cited

U.S. PATENT DOCUMENTS

| | | | |
|---|---|---|---|
| 6,691,946 B2 | 2/2004 | Dannecker et al. | |
| 9,889,462 B2* | 2/2018 | Ahn | B05C 3/08 |
| 10,420,914 B1* | 9/2019 | Koutsouradis | A61M 25/09 |
| 2003/0141407 A1* | 7/2003 | Dannecker | A61B 50/30 |
| | | | 242/588 |
| 2006/0260968 A1* | 11/2006 | Mayda | A61M 25/002 |
| | | | 206/438 |
| 2010/0170816 A1 | 7/2010 | Burgess et al. | |
| 2014/0374295 A1 | 12/2014 | Lessne | |
| 2016/0206394 A1* | 7/2016 | Lampropoulos | B65D 81/22 |
| 2019/0321586 A1* | 10/2019 | Huang | F16L 3/223 |

\* cited by examiner

PLATFORM INSERT FOR BOWL, BOWL WITH PLATFORM, AND METHODS OF USING THE SAME

FIELD OF THE INVENTION

The present invention relates to a filament platform insert for use with endovascular filaments, such as guide wires and catheters, a bowl with such a filament platform inserted therein or formed monolithically therewith, and methods of using the same for storing and extracting endovascular filaments during surgical procedures.

BACKGROUND OF THE INVENTION

Many surgical endovascular procedures are performed with the use of flexible endovascular filaments, such as guide wires and catheters, that serve to introduce and/or remove fluids relative to the patient's body, and/or facilitate insertion and manipulation of other surgical equipment.

When preparing a surgical workspace in advance of a surgical operation endovascular filaments are normally placed in a container filled with a sterile liquid solution. This is done both to maintain sterilization of the filaments and to wet the filaments to facilitate their insertion into the patient's body with minimized irritation to surrounding body tissues. Traditional practice is to use a bowl type container for holding the filaments in a sterile liquid solution, with the filaments coiled around a base of the bowl such that filaments may be readily fed from the bowl as they are inserted into the patient. However, many endovascular filaments are constructed with a stiffness that resists bending and curving, which results in a tendency for the filaments to uncoil in the bowl and press against an inner wall of the bowl with such force as to rise along the wall and spill out of the bowl.

Conventional attempts to overcome this problem of filament rise included the development of specially shaped bowls having barriers placed along the inner surface of the bowl wall so as to act as stops to any filaments that rise along the wall. FIGS. 1-2 show one example of such a conventional endovascular filament bowl 10 (e.g., a guide wire bowl). The conventional bowl 10 includes a vertical wall 11 and a number of barriers 13 that extend radially inward from an inner surface 12 of the wall 11. The barriers 13 each include lower surfaces 14 that act as stops to any filaments that may rise along the vertical wall 11 so as to prevent filaments from rising so far as to spill over an upper rim 15 of the bowl 10. The barriers 13 extend from an elevated surface 17 of a base of the bowl 10, with each elevated surface 17 separated by a cavity surface 16. Further specifics as to the conventional bowl 10 of FIGS. 1-2 are provided in WO 98/56687 (Cude, et al.) and US D433,130 (Cude, et al.), the entire content and disclosure of both of which are hereby incorporated herein by reference.

Though conventional bowls such as that in FIGS. 1-2 have proven successful in facilitating the storage of endovascular filaments, there remains further problems in practices using such conventional bowls. For example, when performing a surgical operation requiring multiple endovascular filaments, storage of the multiple filaments in a single bowl can easily result in the filaments becoming entangled with one another. Untangling the filaments results in lost time that prolongs the surgical operation. Worse yet, there is a risk that entanglement of filaments may result in a spilling of one or more filaments from the bowl, which may potentially contaminate the filaments and/or other nearby equipment in the surgical environment.

Accordingly, there remains a need in the art for means of securely retaining multiple endovascular filaments in a sterile solution within a single container, and for facilitating removal of individual filaments therefrom, while lessening the potential for interference between separate filaments and the potential for mishandling of the filaments as a result thereof.

SUMMARY OF THE INVENTION

A filament platform insert is provided for insertion into a bowl. The platform insert comprises a front end, a rear end, a bottom, a top, a first lateral side, a second lateral side. A plurality of protruding stages and a plurality of protruding recesses are provided on the platform insert, with the stages and recesses alternating in a recess-stage-recess sequence. Stages in the plurality of recesses are defined, at least in part, by a first curved upper surface that slopes vertical upward and radially outward of an edge of the stage, a second straight lower surface that extends radially outwardly horizontally from an edge of the stage, and a third straight intermediate surface that joins the first and second surfaces. Recesses in the plurality of recesses are defined, at least in part, by a first straight upper surface that extends radially inward from an outermost perimeter of the recess, and second curved lower surface that slopes vertically downward and radially inward from the outermost perimeter of the recess. With the recess-stage-recess sequence, a forward most edge of a stage will protrude to a position further radially inward than the outermost perimeter of the preceding recess. The stages and recesses extend between the first and second lateral sides in arcuate shapes centered around a reference axis to form a number of filament channels that likewise extend around between the first and second lateral sides in an arcuate shape centered around the same reference axis.

In a preferred arrangement, the platform is constructed with a staircase configuration in which the stages are positioned sequentially one after another between the front end and the rear end of the platform, and between a bottom and top of the platform, with each successive stage positioned vertically above and radially outward of a preceding stage in both a radially horizontal direction relative to the reference axis and a vertical direction relative to the bottom of the platform; and the recesses are likewise positioned sequentially one after another between the front end and the rear end of the platform, and between a bottom and top of the platform, with each successive recess positioned vertically above and radially outward of a preceding recess in both a radially horizontal direction relative to the reference axis and a vertical direction relative to the bottom of the platform. In this arrangement, the filament channels of the platform, and filament raceways formed by multiple aligned platforms, are arranged in a stepped configuration, with successive channels and raceways positioned further vertically above and radially outward relative to a preceding channel or raceway respectively. With such an arrangement, insertion of multiple platforms into a bowl results in filament raceways that are each at a different radial distance from the reference axis, and each at a different vertical height from the bottom of the bowl.

In an alternative arrangement, the platform may be constructed with a horizontal configuration in which the stages are positioned sequentially one after another between the front end and the rear end of the platform, at a common vertical height, with each successive stage positioned radially outward of a preceding stage in a radially horizontal direction relative to the reference axis; and the recesses are likewise positioned sequentially one after another between the front end and the rear end of the platform, at a common vertical height, with each successive recess positioned radially outward of a preceding recess in a radially horizontal direction relative to the reference axis. In this arrangement, the filament channels of the platform, and filament raceways formed by multiple aligned platforms, are each formed at a common vertical height, with successive channels and raceways positioned further radially outward relative to a preceding channel or raceway respectively. With such an arrangement, insertion of multiple platforms into a bowl results in the filament raceways all being aligned along the base of the bowl, with each raceway having a common height as each other raceway, though each raceway being positioned at a different radial distance from the reference axis.

In another alternative arrangement, the platform may be constructed with a vertical configuration in which the stages are positioned sequentially one after another between the bottom and top of the platform, at a common radial distance from the reference axis, with each successive stage positioned vertically above a preceding stage in a vertical direction relative to the bottom of the platform; and the recesses are likewise positioned sequentially one after another between the bottom and top of the platform, at a common radial distance from the reference axis, with each successive recess positioned vertically above a preceding recess in a vertical direction relative to the bottom of the platform. In this arrangement, the filament channels of the platform, and filament raceways formed by multiple aligned platforms, are each formed at a common radial distance from the reference axis, with successive channels and raceways positioned further vertically upward relative to a preceding channel or raceway respectively. With such an arrangement, insertion of multiple platforms into a bowl results in the filament raceways all being aligned along the wall of the bowl, with each raceway having a common radial distance from the reference axis, though each raceway being positioned at a different vertical height from the bottom of the bowl.

The arcuate shapes of the stages, recesses, and the filament channels formed thereby in platform are non-continuous in that there is provided at least one break in the arcuate shape in the form of an access channel. The access channel extends diagonally along the platform, both in a horizontal sense between the rear end and forward end of the platform and in a vertical sense between the top and the bottom of the platform, the channel being defined at least in part by an opening in each stage in the plurality of stages, the channel openings being positioned between laterally adjacent sections of the arcuate stages, recesses and filament channels.

In use, prior to an operation, a number of filament platforms are inserted at predetermined positions in an endovascular filament bowl so as to align the platforms with one another such that the filament channels of the separate platforms align to form a number of filament raceways. A number of endovascular filaments are then inserted into the filament raceways, preferably with each raceway receiving a single endovascular filament coiled therein. Once the desired number of endovascular filaments are inserted, a sterile solution is introduced into the bowl in sufficient volume to submerse the filaments. Thereafter, during an operation, individual filaments may be extracted from the bowl by grasping the several coils of an individual filament that extend along a single filament raceway, gently applying a radially inwardly directed force to remove the filament from the raceway, and then lifting the grasped filament out of the bowl. Alternatively, if preferring to use the bowl to feed a filament during insertion, a filament may be extracted from the bowl by gripping a coil of an individual filament that is stored in a filament raceway, uncoiling a length of the filament from the raceway, and feeding the filament from the bowl with the filament sliding through the raceway.

In another aspect, the invention is also inclusive of a endovascular filament bowl having the filament platform formed monolithically therein as an integrated component of the bowl.

Both the foregoing general description and the following detailed description are exemplary and explanatory only and are intended to provide further explanation of the invention as claimed. The accompanying drawings are included to provide a further understanding of the invention; are incorporated in and constitute part of this specification; illustrate embodiments of the invention; and, together with the description, serve to explain the principles of the invention.

BRIEF DESCRIPTION OF THE DRAWINGS

Further features and advantages of the invention can be ascertained from the following detailed description that is provided in connection with the drawings described below.

The following disclosure discusses the present invention with reference to the examples shown in the foregoing drawings, though does not limit the invention to those examples.

DETAILED DESCRIPTION OF THE INVENTION

The present invention is inclusive of a filament platform insert for a bowl, an endovascular filament bowl formed with a monolithic filament platform therein, and methods of storing and withdrawn endovascular filaments from a bowl. In the context of this disclosure, endovascular filaments include, though are not limited to, catheters, micro-catheters, guidewires, micro-guidewires, intravenous lines, and similar endovascular equipment.

Figure 3:
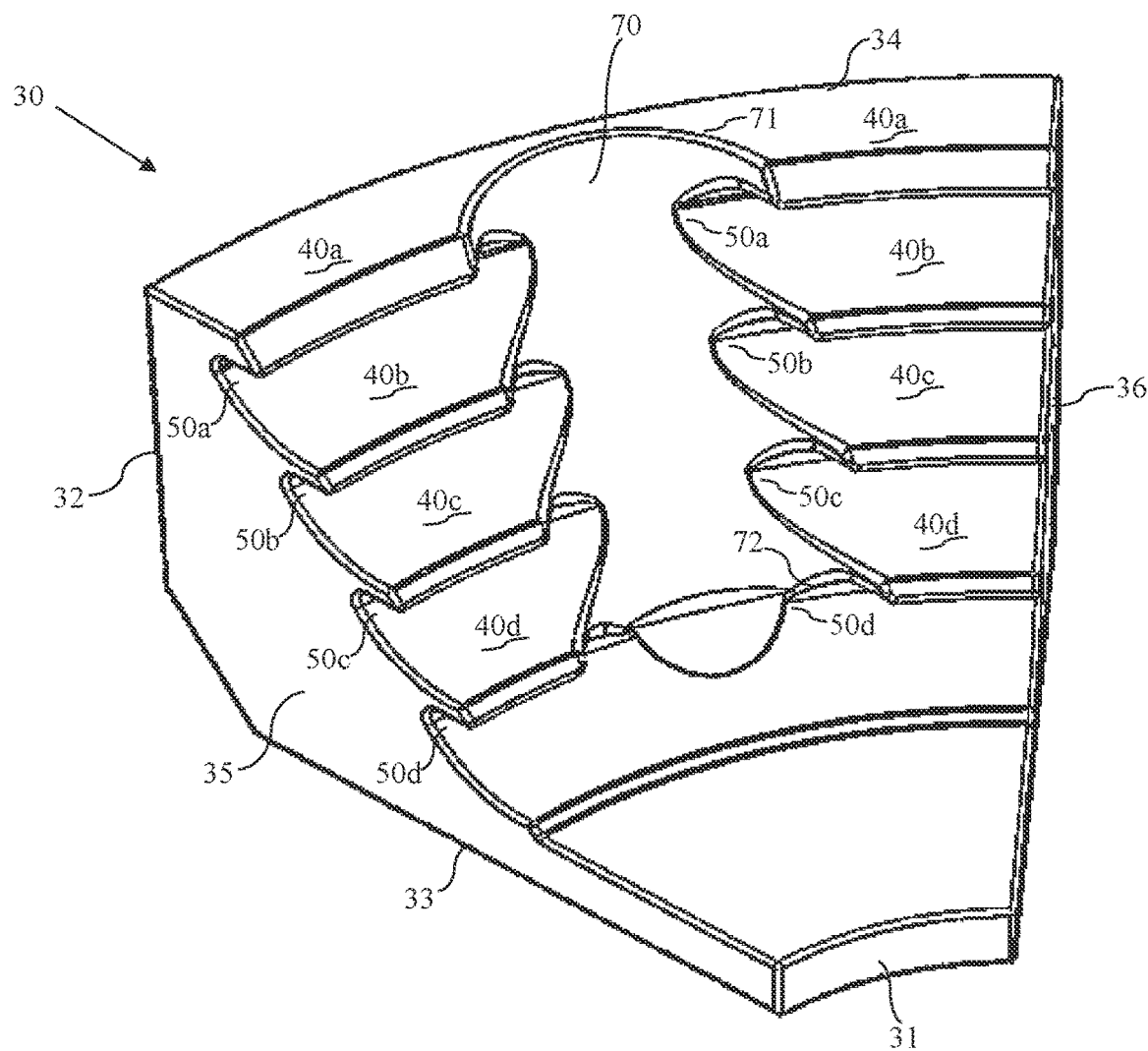
FIG. 3 shows one example of a filament platform according to the present invention.
Figure 4:
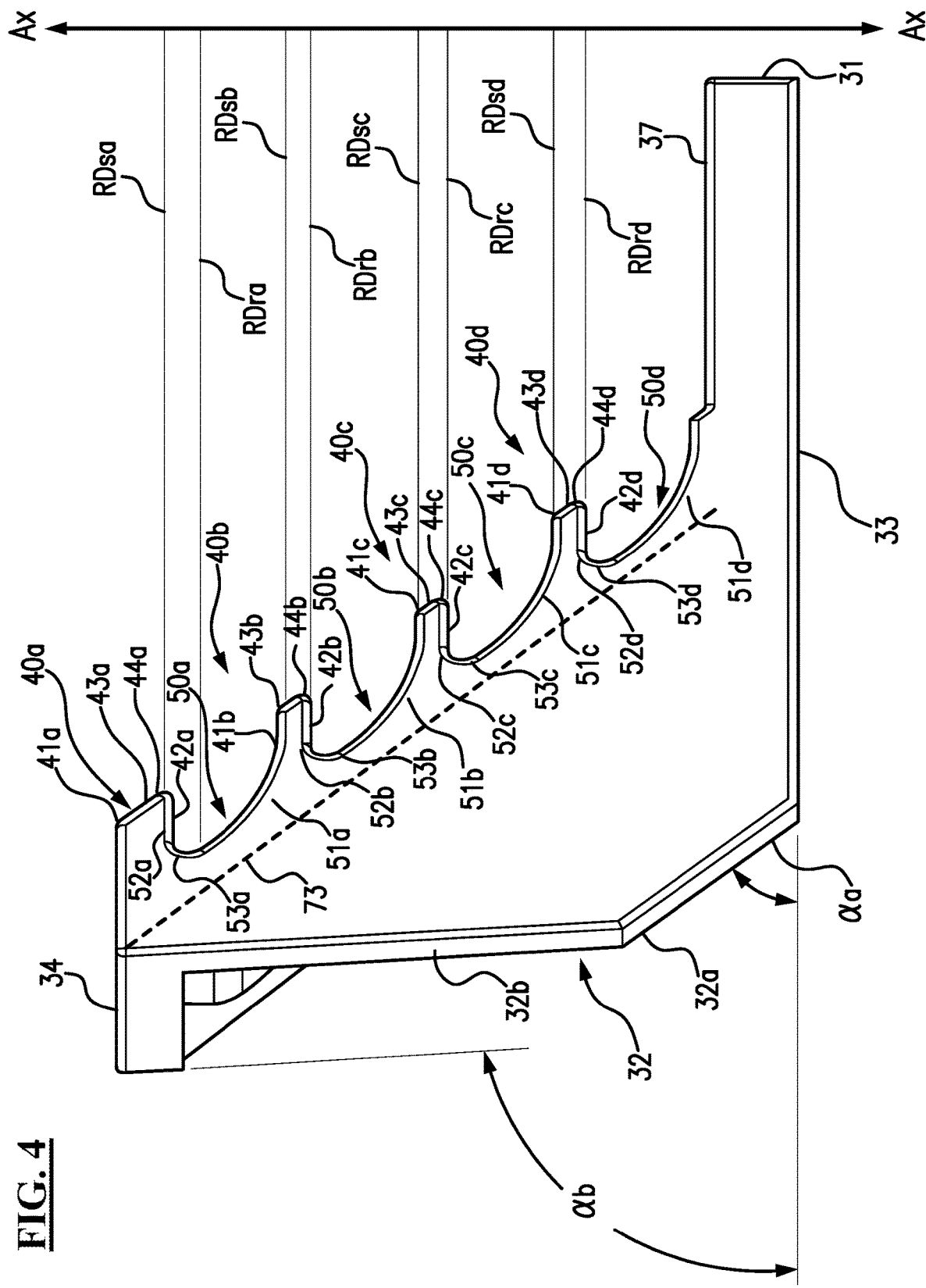
FIG. 4 shows a cross-sectional elevation view of the filament platform of FIG. 1.
Figure 5:
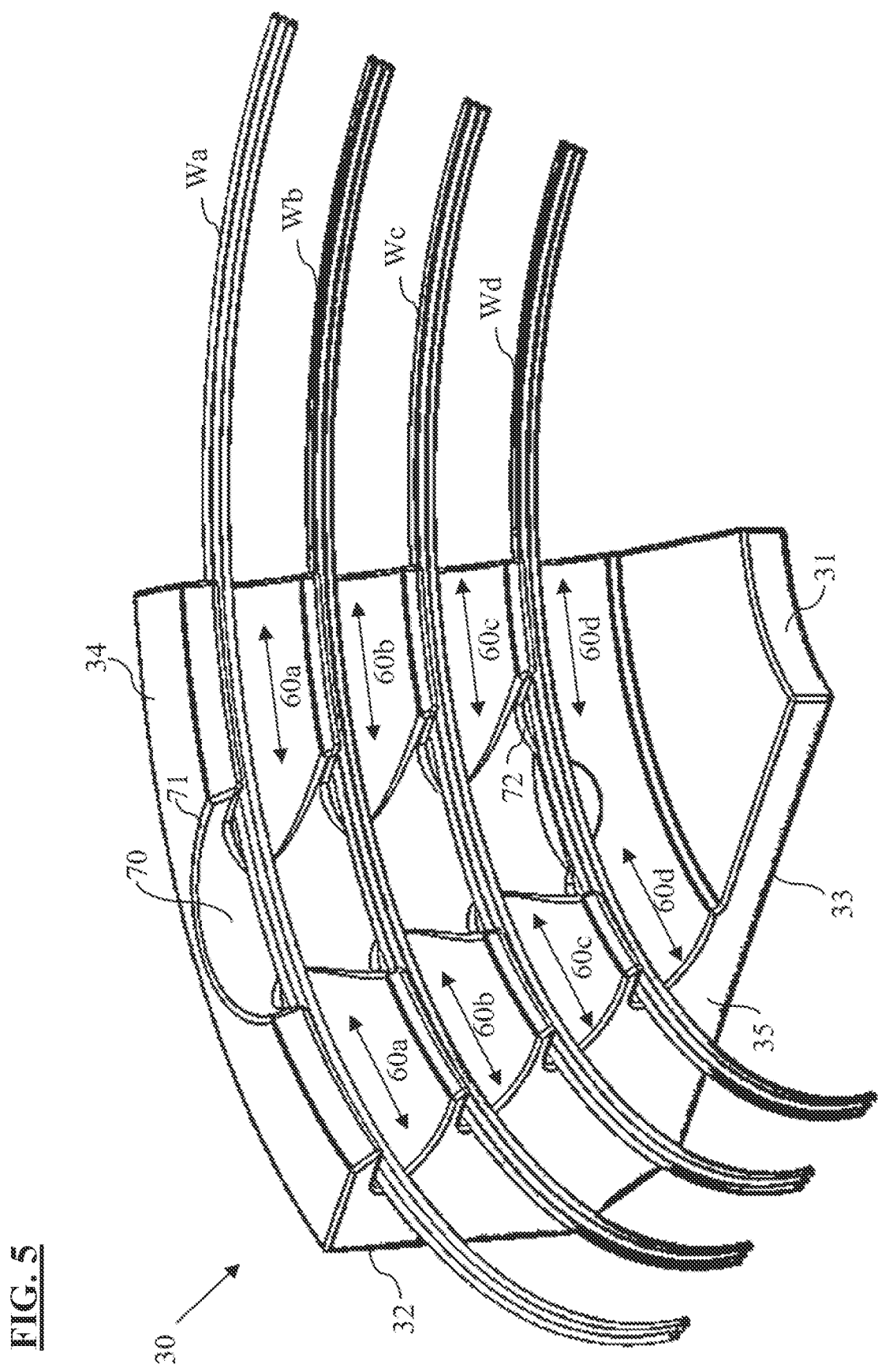
FIG. 5 shows the filament platform of FIG. 1 loaded with a number of endovascular filaments.

FIGS. 3-5 show one example of a platform insert 30 for an endovascular filament bowl having a plurality of stages 40a-40d and recesses 50a-50d. The platform 30 has a front end 31, a rear end 32, a bottom 33, a top 34, a first lateral side 35, and a second lateral side 36. The first and second lateral sides 35/36 extend between the rear end 32 and the front end 31, and taper towards one another. In the illustrated example, the first and second lateral sides 35/36 taper towards one another, but do not meet, and instead terminate at two respective points of the front end 31. Both the rear end 32 and the front end 31 extend from the first lateral side 35 to the second lateral side 36 in an arcuate shape that is circumferentially centered around a vertical reference axis AX positioned forward of the front end 31. In the illustrated example, the arcuate shapes of the rear and front ends 31/32 have a constant radius of curvature along their length, as measured relative to the reference axis AX. In other examples, the first and second lateral sides 35/36 may taper toward one another and meet at a common point, with the front end 31 of the platform 30 being represented by the common point where the two sides meet, and with the vertical reference axis AX passing through that same common point.

In the example shown in FIGS. 3-5, the platform 30 is formed in a staircase shape, with each stage 40a-40d formed as a separate step, and with a corresponding recess 50a-50d below each stage. Each stage 40a-40d and recess 50a-50d extends from the first lateral side 35 to the second lateral side 36 in an arcuate shape that is circumferentially centered around the same vertical reference axis AX as the arcuate shape of the rear and front ends 32/31. In this manner, the several stages 40a-40d are each positioned one behind another in a radial horizontal direction, and one above another in a vertical direction. Likewise, the several recesses 50a-50d are also each positioned one behind another in a radial horizontal direction, and one above another in a vertical direction. The arcuate configurations of the stages and recesses, together, form a number of arcuate filament channels 60a-60d for the reception and storage of coiled endovascular filaments Wa-Wd. In the illustrated example, the arcuate configurations of the stages 40a-40d, recesses 50a-50d and filament channels 60a-60d have a constant radius of curvature, as measured relative to the reference axis AX, though each is formed in non-continuous manner due to the presence of an access channel 70.

As shown in FIG. 4, each stage 40b-40d is defined, at least in part, by a first curved upper surface 41b-41d that slopes upward and radially outward from an edge of the respective stage, a second straight lower surface 42b-42d that extends radially outward from an edge of the respective stage, and a third straight slanted forward surface 43b-43d that extends diagonally to join edges of the respective upper and lower surfaces 41/42. The top-most stage 40a likewise includes a straight lower surface 42a and a straight slanted forward surface 43a, though has a straight upper surface 41a. In other examples, the top-most stage 40a may have a curved upper surface just as each other stage. Each stage 40a-40d extends radially inward from the rear end 32, with each stage 40a-40d having a radially-inward most edge 44 at a different respective radial distance RDs from the reference axis AX. Thus, in the illustrated example with four stages 40a-40d, the radially-inward most edge 44a of the first stage 40a is at a first radial distance RDsa from the reference axis AX; the radially-inward most edge 44b of the second stage 40b is at a second radial distance RDsb from the reference axis AX; the radially-inward most edge 44c of the third stage 40c is at a third radial distance RDsc from the reference axis AX; and the radially-inward most edge 44d of the fourth stage 40d is at a fourth radial distance RDsd from the reference axis AX; with each of the radial distances RDsa-RDsd differing from one another. Though not required, there may be a constant difference in the radial distances of each successive stage.

As shown in FIG. 4, each recess 50a-50d is defined, at least in part, by a first curved lower surface 51 that slopes downward and radially inward from an outward most perimeter 53 of the recess, and a second straight upper surface 52 that extends radially inward from the outward most perimeter 53 of the recess. With the exception of the bottom-most recess 50d, each recess is positioned between two successive stages, with the curved lower surface of a given recess (e.g., 51b/50b) corresponding with the curved upper surface of a first adjacent stage (e.g., 41c/40c), and the straight upper surface of that same given recess (e.g., 52b/50b) corresponding with the straight lower surface of a second adjacent stage (e.g., 42b/40b). The bottom-most recess 50d differs in this regard in that there is no lower stage, and the curved lower surface 51d of the bottom-most recess 50d instead extends from an upper surface 37 of the platform bottom 33. Each recess 50a-50d extends radially outward from the reference axis AX and toward the rear end 32 of the platform 30, with each recess 50a-50d extending a different respective radially distance RDr such that a radially-outward most perimeter 53a-53d of each respective recess 50a-50d is at a different respective radial distance RDr from the reference axis AX. Thus, in the illustrated example with four recesses 50a-50d, the radially-outward most perimeter 53a of the first recess 50a is at a first radial distance RDra from the reference axis AX; the radially-outward most perimeter 53b of the second recess 50b is at a second radial distance RDrb from the reference axis AX; the radially-outward most perimeter 53c of the third recess 50c is at a third radial distance RDrc from the reference axis AX; and the radially-outward most perimeter 53d of the fourth recess 50d is at a fourth radial distance RDrd from the reference axis AX; with each of the radial distances RDra-RDrd differing from one another. Though not required, there may be a constant difference in the radial distances of each successive recess.

Figure 1:
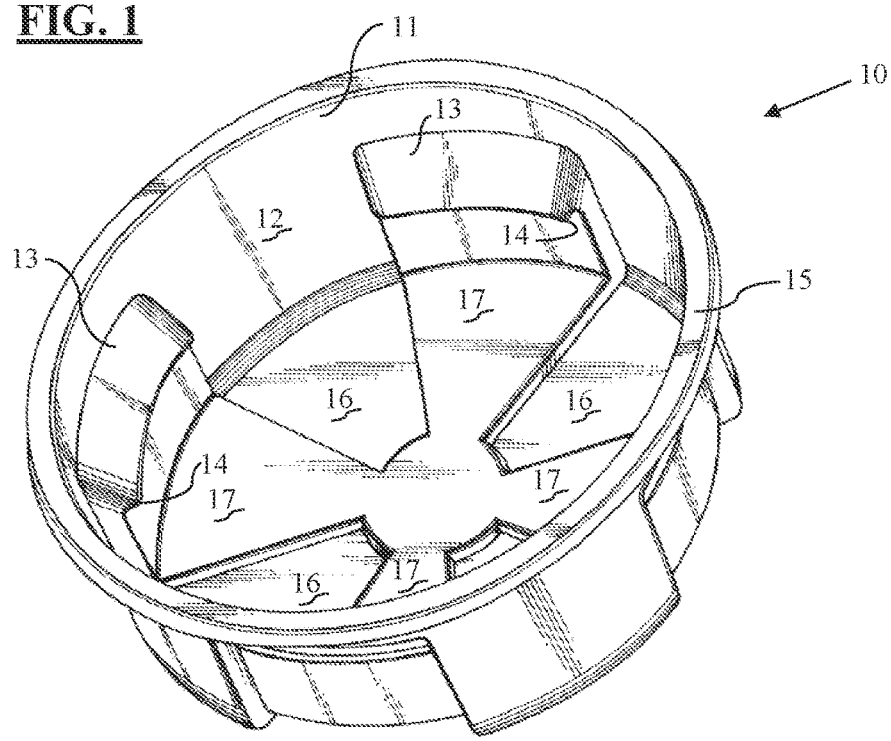
FIG. 1 shows one example of a conventional endovascular filament bowl.
Figure 2:
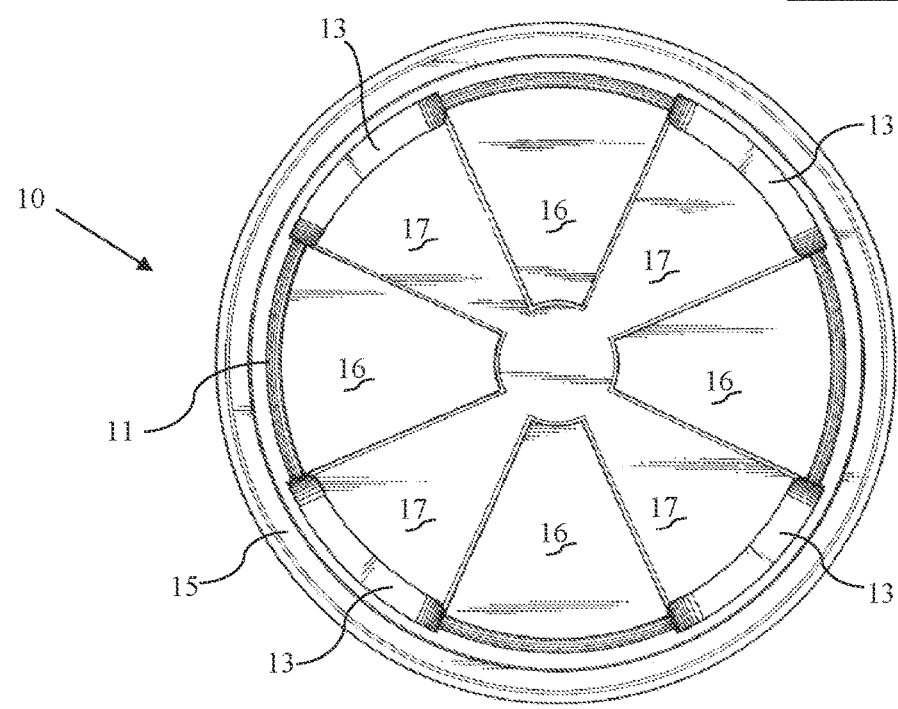
FIG. 2 shows a top plan view of the conventional endovascular filament bowl of FIG. 1.

It is noted that in the example shown in FIG. 4 the rear end 32 is formed of a first wall 32a at a first angle $\alpha$a and a second wall 32b at a second angle $\alpha$b. In the illustrated example, the first and second walls 32a and 32b, as well as the first and second angles $\alpha$a and $\alpha$b, are set to correspond with the inner wall surfaces of the endovascular filament bowl 10 shown in FIGS. 1-2. In other examples, the rear end walls 32a and 32b may be set at any other angles for aligning with a bowl having differently angled inner walls, and may also be provided in other configurations so as to correspond with bowls having differently shaped inner walls. For example, the first rear wall 32a may be constructed with a curved surface having a radius of curvature to correspond with a bowl having an inner wall with a corresponding curvature at its base. In another example, the rear wall 32 may be constructed with only a single wall that extends directly vertically from a 90° angle formed with the bottom 33 of the platform, so as to correspond with a bowl having a similar 90° angle between an inner wall and an inner base.

As seen in FIGS. 3 and 5, the arcuate shapes of the stages 40a-40d, recesses 50a-50d, and filament channels 60a-60d are non-continuous in that there is provided a break in the arcuate shapes in the form of an access channel 70 that passes through each stage and recess. The access channel 70 extends from a top opening 71 in the upper surface 41a of the top-most stage 40a through a bottom opening 72 in the lower surface 42d of the bottom-most stage 40d, and down to the lower curved surface 51d of the bottom-most recess 50d. In the illustrated example, as the platform 30 is formed with the staircase configuration, the access channel 70 is made to extend in an angled fashion, so as to extend downward and forward from the top opening 71 through the lower opening 72. As shown in FIG. 4, a radially outward most perimeter 73 of the access channel 70 is positioned further radially outward than the radially outward most perimeters 503a-53d of each corresponding recess 50a-50d, such that there is provided a clearance space between the access channel 70 and a resting position of a filament Wa-Wd in each respective filament channel 60a-60d.

Figure 6:
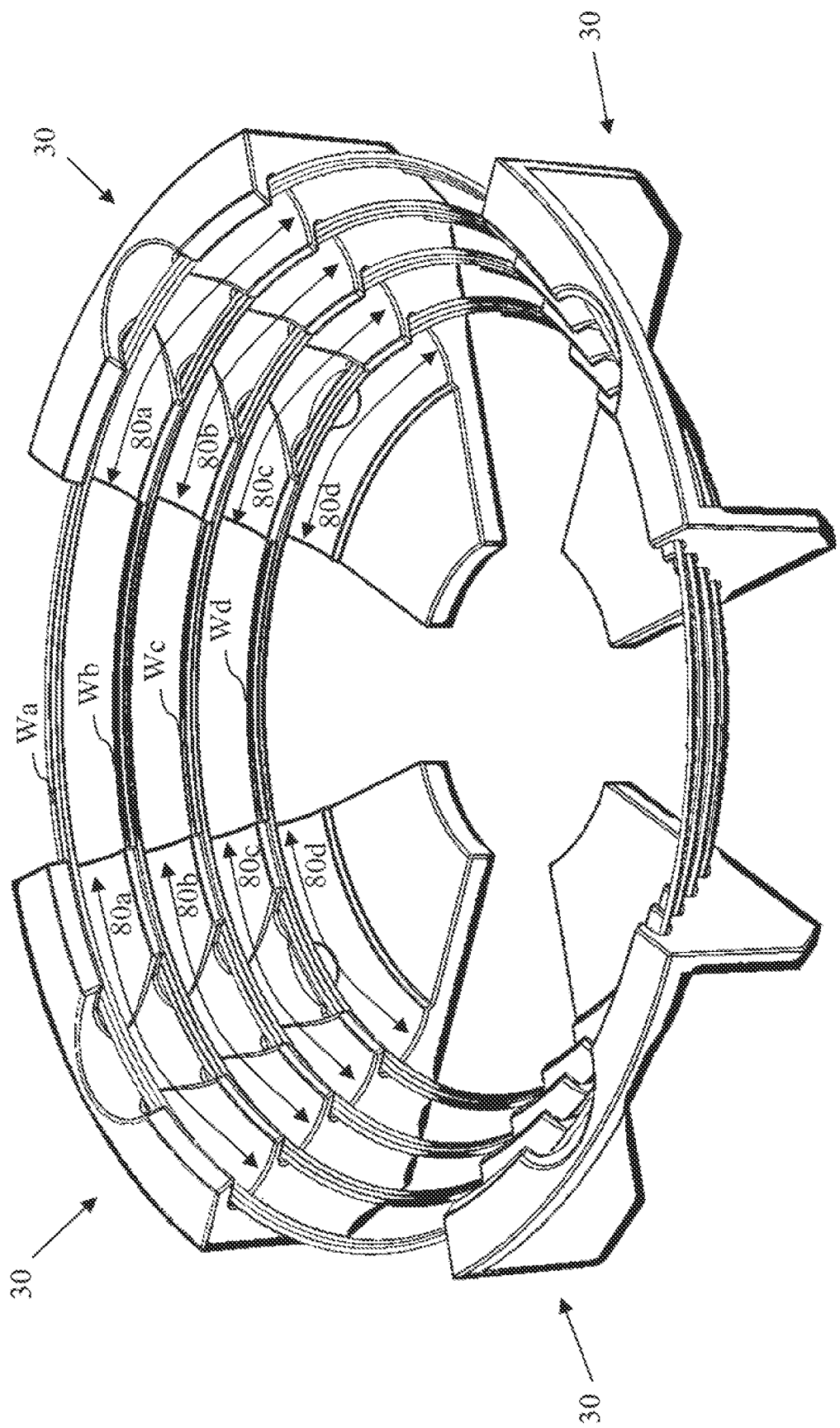
FIG. 6 shows multiple filament platforms according to FIG. 1 aligned to form filament raceways loaded with a number of endovascular filaments.

As shown in FIG. 6, the arcuate shapes of the stages 40a-40d, the recesses 50-50d and the filament channels 60-60d in a platform 30 is adapted such that when a number of the platforms 30 are aligned at predetermined positions relative to one another the guide channels 60a-60d of the aligned platforms 30 form a series of filament raceways 80a-80d that each defined a circumferential path for reception of a coiled filament Wa-Wd, with each raceway 80a-80d separated from another by a stage. In the illustrated example, as the platforms 30 are each formed with the staircase configuration, the successive raceways 80a-80b are each positioned one behind another in a radial horizontal direction, and one above another in a vertical direction.

Figure 7:
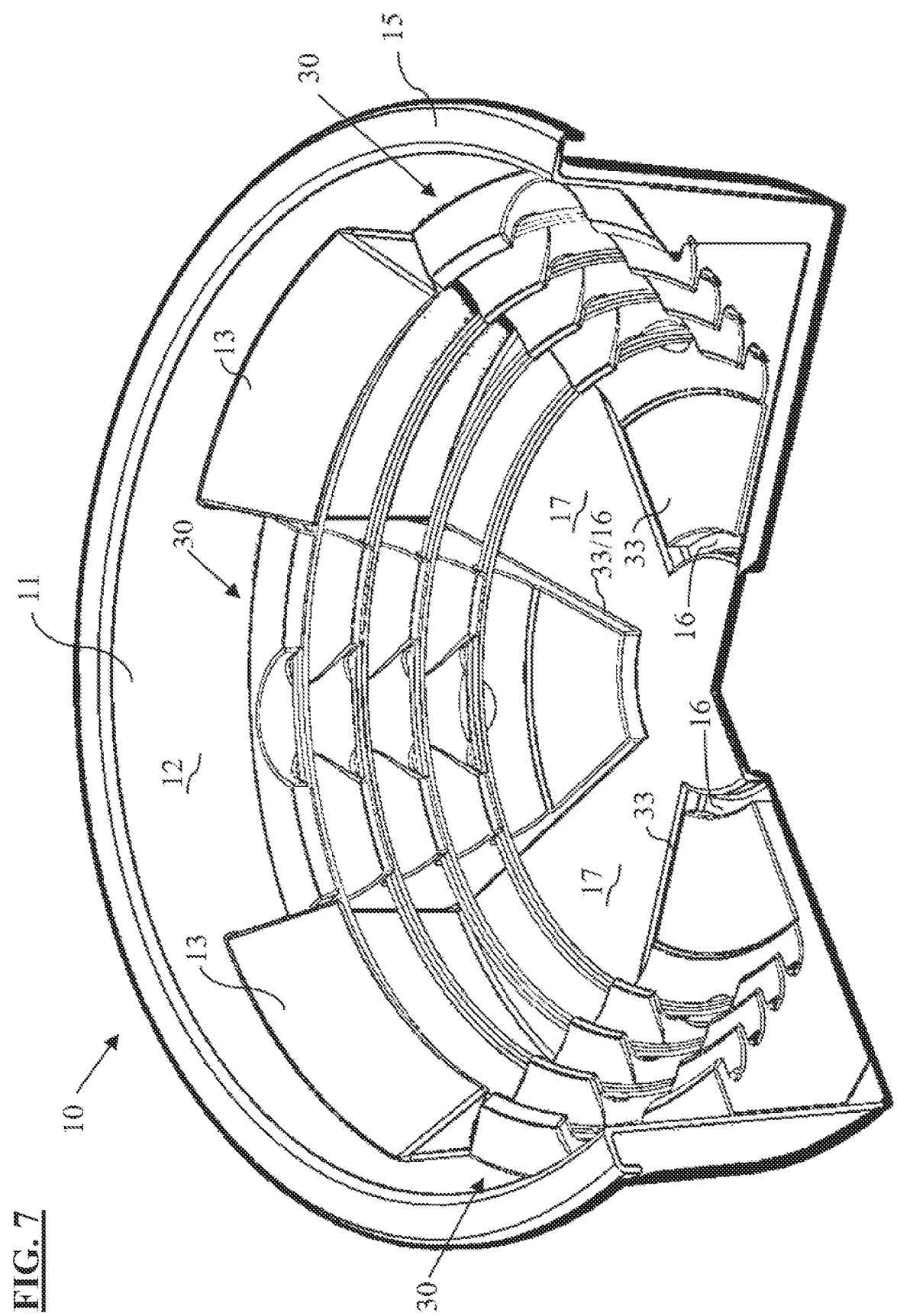
FIG. 7 shows multiple filament platforms according to FIG. 1 aligned to form filament raceways loaded with a number of endovascular filaments, with the filament platforms inserted in an endovascular filament bowl.

As shown in FIG. 7, the bottom 33 of the platform 30 in this example is shaped and dimensioned for insertion into a cavity 16 of the bowl 10, and the arcuate shape of the rear end 32 is adapted to align with the inner surface 12 of the side wall 11 thereof, such that four platforms 30 may be inserted into a single bowl 10 so as to form four circular filament raceways 80-80d for reception and storage of four different filament Wa-Wd. The platform 30 is constructed with such a height that a filament Fa held in the top-most filament raceway 80a will remain below the lower surfaces 14 of the barriers 13.

In use, prior to a surgical procedure, a number of platforms 30 are inserted into a bowl 10 at positions relative to one another to form a number of filament raceways 80a-80d within the bowl 10. Endovascular filaments Wa-Wd are then inserted into and coiled around the separate filament raceways 80-80d, preferably with each raceway receiving a single filament. After all filaments Wa-Wd have been coiled into the raceways 80a-80d, a sterile liquid solution is then introduced to the bowl 10 in sufficient volume to submerse the filaments Wa-Wd.

Subsequently, during the surgical procedure, a user may extract a filament from a filament raceway by inserting and sliding a finger (or a tool) into and through the access channel 70 in a platform 30. The spacing provided between the outward most perimeter 73 of the access channel 70 and the outward most perimeters 53a-53d of the corresponding recesses 50a-50d provides ample clearance for the user's finger (or tool) to slide behind the filaments Wa-Wd held in the respective raceways 80a-80d to facilitate easy manipulation of each coiled filament. Once a filament is gripped through the access channel 70, the user may either extract that filament in its entirety, or may uncoil a single loop of that filament and proceed to feed the filament from the bowl 10 for insertion into a patient's body. Advantageously, the circular configuration of the raceways 80a-80d, combined with the separation provided between each by the plurality of stages 40a-40d, facilitates circular revolutions of filament in the raceways that further promotes feeding of individual filaments without interference between separate filament.

It will be readily appreciated that the construction of the platform insert 30, and the raceways 80a-80d that are formed from the alignment of multiple such platforms 30, provides an improved structure for the storage and extraction of endovascular filaments, whereby multiple individual endovascular filaments may be securely retained independent of one another in a single bowl 10, without risk of entanglement, while at the same time promoting simplified extraction of individual filaments in a manner to facilitate feeding of filaments during a surgical procedure.

Although the present invention is described with reference to particular embodiments, it will be understood to those skilled in the art that the foregoing disclosure addresses exemplary embodiments only; that the scope of the invention is not limited to the disclosed embodiments; and that the scope of the invention may encompass additional embodiments embracing various changes and modifications relative to the examples disclosed herein without departing from the scope of the invention as defined in the appended claims and equivalents thereto.

For example, though the foregoing discussion and the accompanying drawings illustrate an example wherein four filament platforms are inserted into a bowl 10, it will be understood that the invention may be practiced with fewer than four platforms inserted into the bowl 10, such as methods where three, two or even a single platform are inserted. The invention may also be practiced with bowls of different shapes and dimensions than the endovascular filament bowl 10, with the individual platforms being formed with corresponding shapes and dimensions for that alternative bowl (e.g., differently shaped rear ends, which may have a different curvature or no curvature at all in the instance of a square or rectangular bowl). The platforms may also be used in bowls that lack any other endovascular filament structures therein (e.g., omitting structures such as the elevated surfaces 17 and barriers 13 of endovascular filament bowl 10), in which instances the filament platforms may be constructed to occupy a greater volume of the bowl (e.g., individual platforms may be formed as half-circle insets with two inserts filling the bowl, or even as a full circle insert with a single insert filling the bowl). Similarly, though the foregoing examples illustrate the filament raceways being formed in a circular shape, the raceways may be formed in other shapes, including an oval shape.

Figure 8:
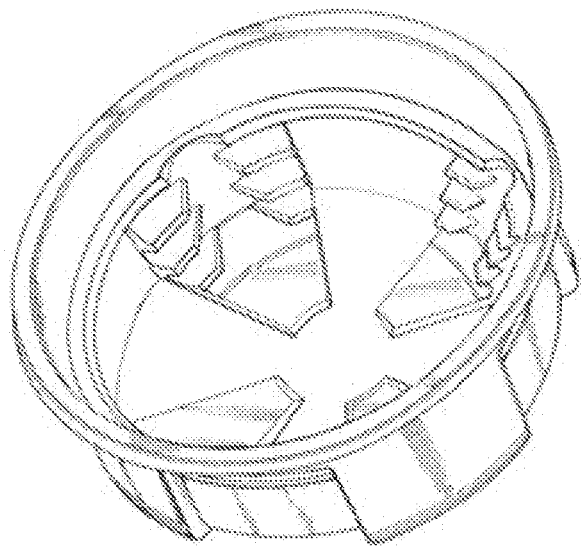
FIG. 8 shows a endovascular filament bowl with the filament platform of FIG. 1 formed monolithically therein.
Figure 9:
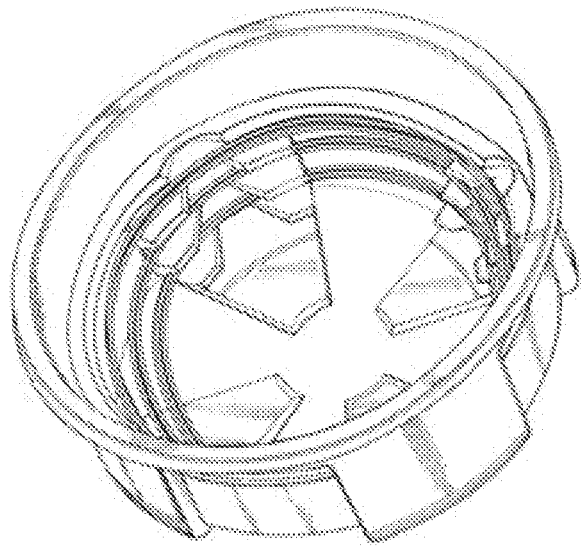
FIG. 9 shows the monolithically formed endovascular filament bowl of FIG. 8 loaded with endovascular filaments.

Also, though the foregoing discussion addresses examples wherein the filament platform is made as a separate insert for insertion into a bowl, the invention is also inclusive of an endovascular filament bowl having the platforms formed monolithically therein as integrated components of the bowl, with such a monolithically constructed bowl optionally including or omitting the barriers 13 that are provided in endovascular filament bowl 10, as illustrated in FIGS. 8-9.

In addition, though the foregoing examples illustrate the platforms as having four stages and recesses, forming four raceways, the platforms may have any number of stages and recesses for forming any number of recesses, including a single stage and recess for forming a single raceway.

Furthermore, through the foregoing examples illustrate the platform being constructed with a staircase configuration, the platform may instead be constructed with other configurations. For example, the platform may be constructed with a horizontal configuration in which successive stages, recesses, and filament channels are each positioned one behind another in a radial horizontal direction, though each at the same height as one another, such that insertion of a plurality of platforms into a bowl will form filament raceways that are all aligned horizontally along the base of the bowl, with each raceway having a common height, though positioned at a different radial distance from the reference axis. In another example, the platform may be constructed in a vertical configuration in which successive stages, recesses, and filament channels are each positioned one above another in a vertical direction, though each at the same radial distance from the reference axis as one another, such that insertion of a plurality of platforms into a bowl will form filament raceways that are all aligned vertically along the wall of the bowl, with each raceway having a common radial distance from the reference axis, though positioned at a different vertical heights from the bottom of the bowl.

To the extent necessary to understand or complete the disclosure of the present invention, all publications, patents, and patent applications mentioned herein are expressly incorporated by reference herein to the same extent as though each were individually so incorporated.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the embodiments herein have other applications in other environments. This application is intended to cover any adaptations or variations of the present disclosure.

The present invention is not limited to the exemplary embodiments illustrated herein, but is instead characterized by the appended claims, which do not themselves in any way limit the scope of the foregoing disclosure.

What is claimed is:

1. A filament bowl comprising
 a filament platform, the filament platform comprising:
  a platform body having an arcuate shape with a front end, a rear end, a bottom, a top, a first lateral side, and a second lateral side, the first and second lateral sides extending vertically between the bottom and top, the front end extending laterally between the first and second lateral sides at a radially-inward perimeter between the bottom and top, and the rear end extending laterally between the first and second lateral sides at a radially-outward perimeter between the bottom and top;
  the platform body comprising a plurality of stages that protrude in a radially-inward direction, with at least one stage in the plurality of stages being defined at least in part by a first upper surface and a second lower surface, and a plurality of recesses that are open at a radially-inward side of the platform and extend into the platform body in a radially-outward direction, with at least one recess in the plurality of recesses being defined at least in part by a first curved radially-outward surface and a second upper surface, the plurality of stages and recesses forming a plurality of filament channels in the platform body, wherein
   the plurality of stages and the plurality of recesses are arranged in a recess-stage-recess sequence, with at least one sequence in which the second upper surface of a recess corresponds with the second lower surface of an adjacent platform and the first curved radially-outward surface of the recess has a radially-outward most point at an upper end of the curved surface, and
   stages in the plurality of stages and recesses in the plurality of recesses extend laterally between the first lateral side and the second lateral side such that the arcuate shape of the platform body is circumferentially centered around a reference axis that extends in a top-to-bottom direction, perpendicular to the lateral extension of the stages and recesses, with the reference axis passing through a point at or forward of the front end of the platform body.

2. The filament bowl according to claim 1, wherein
the filament platform is a monolithic component of the filament bowl.

3. The filament bowl according to claim 1, wherein
the stages in the plurality of stages are positioned sequentially one after another between the front end and the rear end of the platform body, with successive stages positioned radially outward of a preceding stage in a radially horizontal direction relative to the reference axis, and
the recesses in the plurality of recesses are positioned sequentially one after another between the front end and the rear end of the platform body, with successive recesses positioned radially outward of a preceding recess in a radially horizontal direction relative to the reference axis.

4. The filament bowl according to claim 3, wherein
in the recess-stage-recess sequence of the plurality of stages and the plurality of recesses, a forward most edge of a stage that is positioned radially outward of a preceding recess extends to a position that is further radially inward than a position of a radially outward most perimeter of the preceding recess.

5. The filament bowl according to claim 3, wherein
the arcuate shapes of the stages and recesses, and the filament channels formed thereby, extend non-continuously between the first lateral side and the second lateral side.

6. The filament bowl according to claim 5, further comprising
a channel extending at least in part horizontally between the rear end and the front end of the platform body in the radially horizontal direction, the channel being defined at least in part by openings in stages in the plurality of stages, the channel openings being positioned between laterally adjacent sections of filament channels.

7. The filament bowl according to claim 1, wherein
the stages in the plurality of stages are positioned sequentially one after another between the bottom and the top of the platform body, with successive stages positioned above a preceding stage in a vertical direction relative to the bottom of the platform, and
the recesses in the plurality of recesses are positioned sequentially one after another between the bottom and the top of the platform body, with successive recesses positioned above a preceding recess in a vertical direction relative to the bottom of the platform.

8. The filament bowl according to claim 7, wherein
in the recess-stage-recess sequence of the plurality of stages and the plurality of recesses, a forward most edge of a stage that is positioned vertically above a preceding recess extends to a position that is further radially inward than a position of a radially outward most perimeter of the preceding recess.

9. The filament bowl according to claim 7, wherein
the arcuate shapes of the stages and recesses, and the filament channels formed thereby, extend non-continuously between the first lateral side and the second lateral side.

10. The filament bowl according to claim 9, further comprising
a channel extending at least in part vertically between the top of the platform body and the bottom of the platform body in the vertical direction, the channel being defined at least in part by openings in stages in the plurality of stages, the channel openings being positioned between laterally adjacent sections of filament channels.

11. The filament bowl according to claim 1, wherein
the platform body is formed with a staircase configuration such that
the stages in the plurality of stages are positioned sequentially one after another between the bottom and the top of the platform body and between the front end and the rear end of the platform body, which successive stages positioned vertically above a preceding stage in a vertical direction relative to the bottom of the platform body and radially outward of the preceding stage in a horizontal direction relative to the reference axis, and
the recesses in the plurality of recesses are positioned sequentially one after another between the bottom and the top of the platform body and between the front end and the rear end of the platform body, which successive recesses positioned vertically above a preceding recess in a vertical direction relative to the bottom of the platform body and radially outward of the preceding recess in the horizontal direction relative to the reference axis.

12. The filament bowl according to claim 11, wherein
in the recess-stage-recess sequence of the plurality of stages and the plurality of recesses, a forward most edge of a stage that is positioned vertically above and radially outward of a preceding recess extends to a position that is further radially inward than a position of a radially outward most perimeter of the preceding recess.

13. The filament bowl according to claim 11, wherein
the arcuate shapes of the stages and recesses, and the filament channels formed thereby, extend non-continuously between the first lateral side and the second lateral side.

14. The filament bowl according to claim 13, further comprising
a channel extending diagonally along the platform body, so as to extend in part vertically between the top of the platform and the bottom of the platform body and in part horizontally between the rear end and the front end of the platform body, the channel being defined at least in part by openings in stages in the plurality of stages, the channel openings being positioned between laterally adjacent sections of filament channels.

15. The filament bowl according to claim 1, wherein
recesses in the plurality of recesses are configured such that filaments retained in the recesses remain exposed for removal from the recesses by translating the filament in a radially inward direction, toward the reference axis, and out the recessing openings at the radially-inward side of the platform.

16. A method of using endovascular filaments in a surgical procedure, comprising
inserting at least one endovascular filament into a filament raceway that is formed from alignment of filament channels of two or more filament platforms in a filament bowl according to claim 1, with the endovascular filament extending along the filament raceway so as to be held in a coiled arrangement within the filament bowl;
introducing a sterile solution into the filament bowl in sufficient volume to submerse the at least one endovascular filament.

17. The method of claim 16, further comprising
extracting an endovascular filament from the filament bowl by gripping the endovascular filament coiled in a filament raceway, uncoiling a length of the endovascular filament from the filament raceway, and feeding the gripped endovascular filament from the filament bowl with the endovascular filament sliding through the filament raceway.

18. The method of claim 17, wherein
at least one filament platform in the filament bowl further comprises an access channel that extends horizontally between the rear end and the front end of the platform body, vertically between the top and the bottom of the platform body, or both horizontally and vertically, the channel being defined at least in part by access openings in individual stages in the plurality of stages, with the access openings being positioned between laterally adjacent sections of filament channels, and
gripping an endovascular filament in a filament raceway for extraction from the filament bowl comprises inserting a user's finger or a tool along the access channel so as to engage a length of the endovascular filament that is exposed at an access opening.

19. The method of claim 16, wherein
the at least one endovascular filament inserted into a filament raceway is a catheter, a micro-catheter, a guidewire, a micro-guidewire, or an intravenous line.

* * * * *